(12) United States Patent
Menn et al.

(10) Patent No.: US 11,583,293 B2
(45) Date of Patent: *Feb. 21, 2023

(54) HEMOSTATIC CLIPPING DEVICES AND METHODS

(71) Applicant: Boston Scientific Scimed, Inc., Maple Grove, MN (US)

(72) Inventors: Dmitri Menn, Marblehead, MA (US); Russell F. Durgin, Bellingham, MA (US); Brian Keith Wells, LaGrange, KY (US); Lance Alan Wolf, Madison, AL (US); Gregory R. Furnish, Louisville, KY (US); Vasiliy P. Abramov, Louisville, KY (US); William C. Mers Kelly, Crestwood, KY (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 324 days.

This patent is subject to a terminal disclaimer.

(21) Appl. No.: 16/949,118

(22) Filed: Oct. 14, 2020

(65) Prior Publication Data
US 2021/0022747 A1    Jan. 28, 2021

Related U.S. Application Data

(63) Continuation of application No. 16/195,912, filed on Nov. 20, 2018, now Pat. No. 10,835,261, which is a
(Continued)

(51) Int. Cl.
*A61B 17/128* (2006.01)
*A61B 17/122* (2006.01)
(Continued)

(52) U.S. Cl.
CPC .... *A61B 17/1285* (2013.01); *A61B 17/00234* (2013.01); *A61B 17/083* (2013.01);
(Continued)

(58) Field of Classification Search
CPC .............. A61B 17/1285; A61B 17/083; A61B 17/00234; A61B 17/10; A61B 17/122; A61B 2017/00778; A61B 2090/037
See application file for complete search history.

(56) References Cited

U.S. PATENT DOCUMENTS 3,958,576 A * 5/1976 Komiya ................. A61B 17/10
24/537
6,814,742 B2 * 11/2004 Kimura .............. A61B 17/1285
606/151
(Continued)

*Primary Examiner* — Julian W Woo
(74) *Attorney, Agent, or Firm* — Fay Kaplun & Marcin, LLP

(57) ABSTRACT

A tissue clipping apparatus, comprises a flexible, elongate member, a proximal end of which remains external to the body accessible to a user while a distal end of the flexible member is inserted into the body to a location adjacent to target tissue to be clipped and a control wire extending through the flexible member in combination with a capsule releasably coupled to a distal end of the flexible member and a clip a proximal portion of which is received within the capsule. A joint releasably coupling the clip to the control wire, includes a yoke extending around a proximal end of the clip and a frangible link which fails when subject to a predetermined force to separate the clip from the control wire.

15 Claims, 11 Drawing Sheets

Related U.S. Application Data continuation of application No. 15/097,896, filed on Apr. 13, 2016, now Pat. No. 10,166,028, which is a continuation of application No. 14/159,993, filed on Jan. 21, 2014, now Pat. No. 10,595,877, which is a continuation of application No. 12/485,542, filed on Jun. 16, 2009, now Pat. No. 8,663,247.

(60) Provisional application No. 61/074,094, filed on Jun. 19, 2008.

(51) Int. Cl.
*A61B 17/10* (2006.01)
*A61B 17/00* (2006.01)
*A61B 17/08* (2006.01)
*A61B 90/00* (2016.01)

(52) U.S. Cl.
CPC ............ *A61B 17/10* (2013.01); *A61B 17/122* (2013.01); *A61B 2017/00778* (2013.01); *A61B 2090/037* (2016.02)

(56) References Cited

U.S. PATENT DOCUMENTS

| | | | | |
|---|---|---|---|---|
| 7,879,052 | B2* | 2/2011 | Adams | A61B 17/1285 606/157 |
| 8,308,743 | B2* | 11/2012 | Matsuno | A61B 17/1285 606/151 |
| 8,551,119 | B2* | 10/2013 | Kogiso | A61B 17/1227 606/143 |
| 8,900,254 | B2* | 12/2014 | Kobayashi | A61B 17/1227 606/139 |
| 10,835,261 | B2* | 11/2020 | Menn | A61B 17/122 |

\* cited by examiner

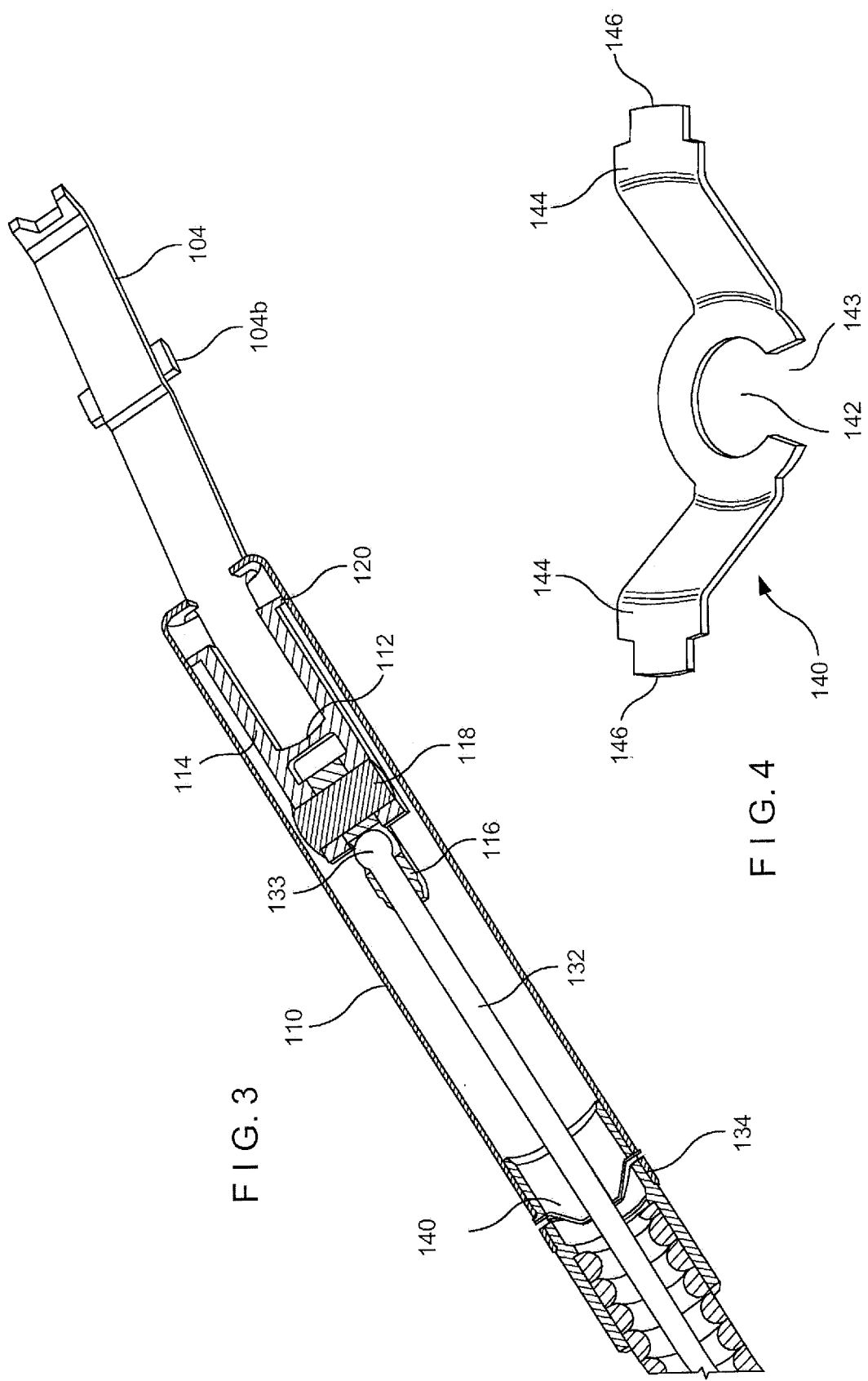

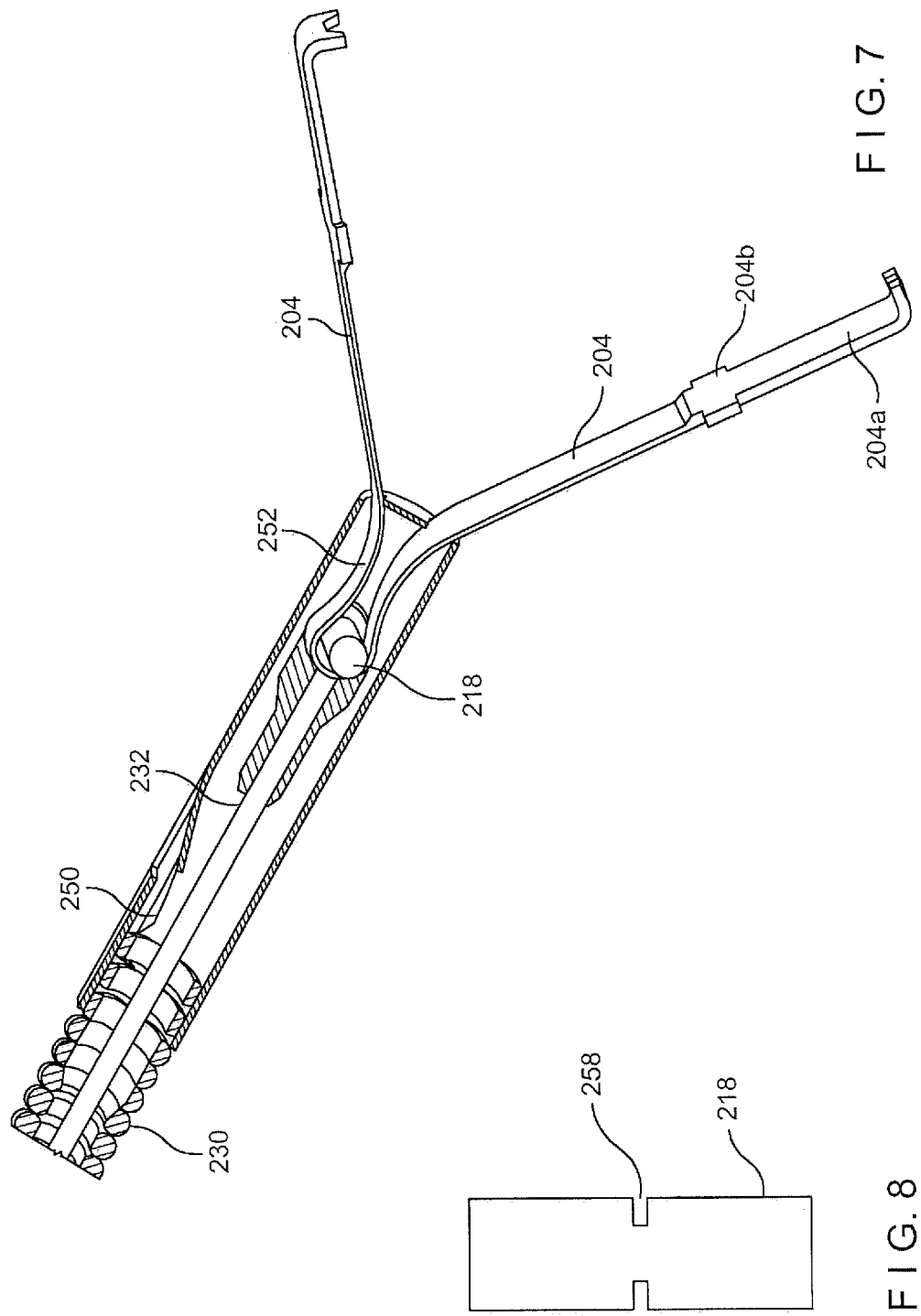

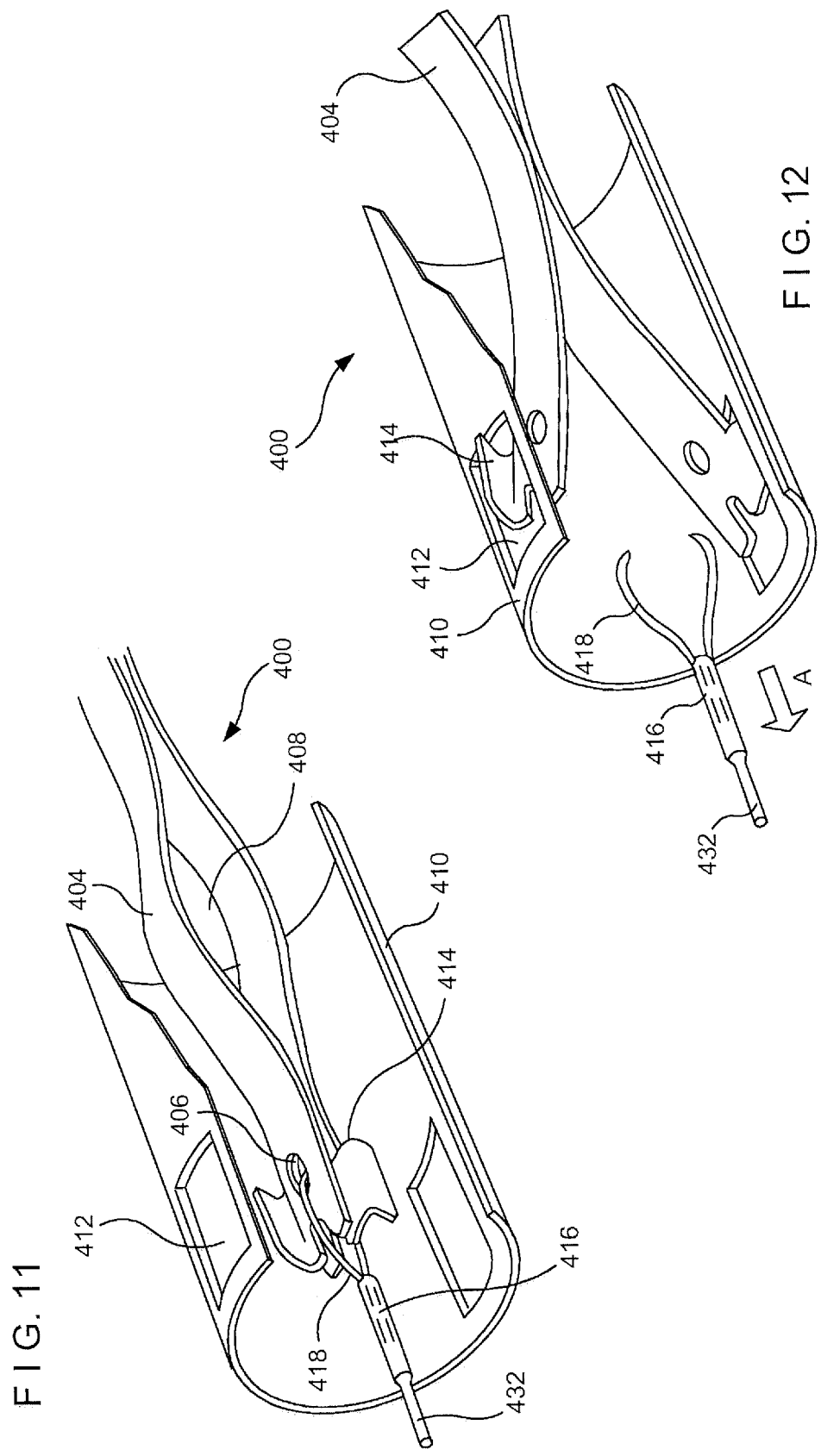

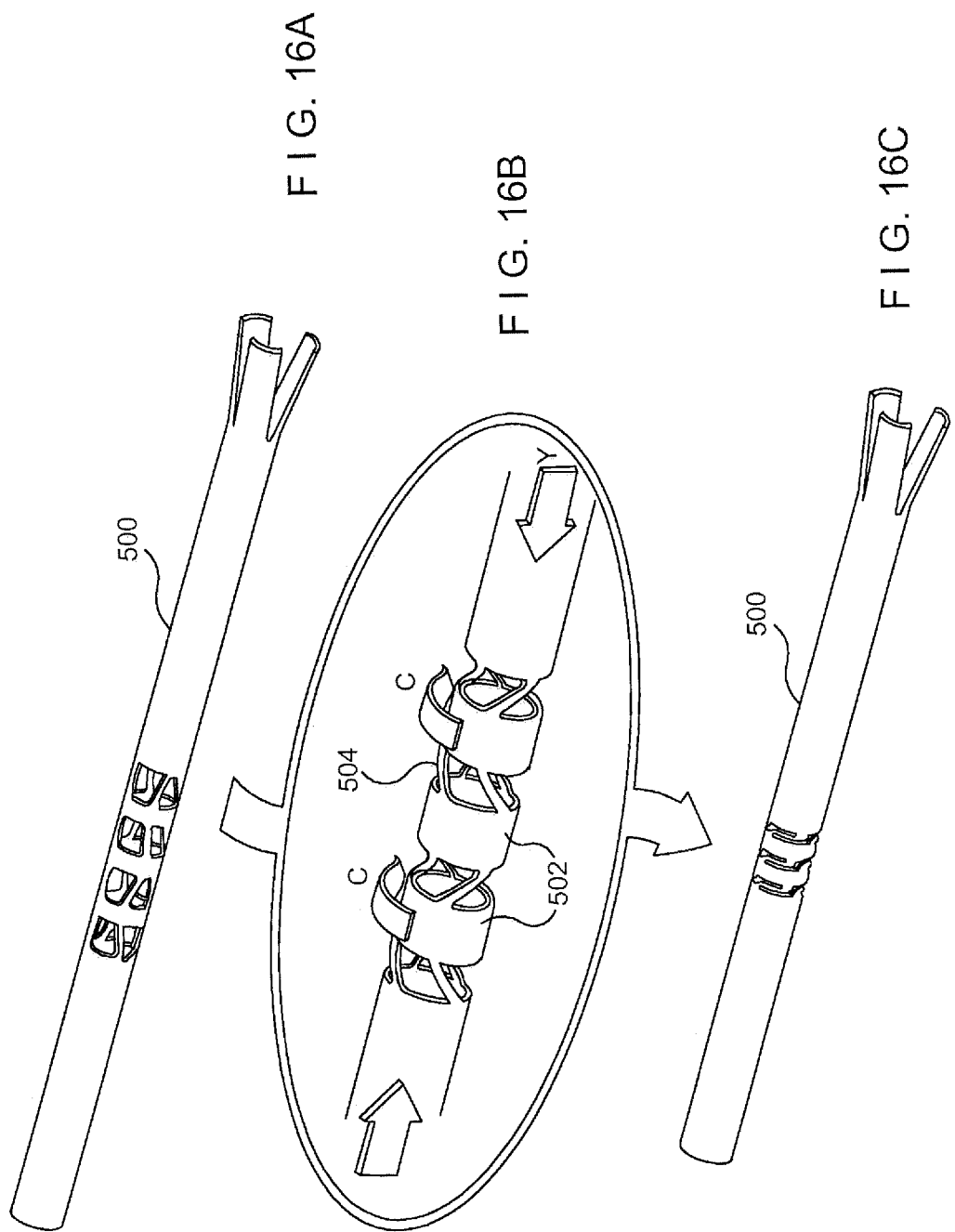

HEMOSTATIC CLIPPING DEVICES AND METHODS

PRIORITY CLAIM

The present application is a Continuation of U.S. patent application Ser. No. 16/195,912 filed on Nov. 20, 2018, now U.S. Pat. No. 10,835,261; which is Continuation of U.S. patent application Ser. No. 15/097,896 filed on Apr. 13, 2016, now U.S. Pat. No. 10,166,028; which is a Continuation of U.S. patent application Ser. No. 14/159,993 filed on Jan. 21, 2014, now U.S. Pat. No. 10,595,877; which is a Continuation of U.S. patent application Ser. No. 12/485,542 filed on Jun. 16, 2009, now U.S. Pat. No. 8,663,247; which claims priority to U.S. Provisional Application Ser. No. 61/074,094 filed on Jun. 19, 2008. The entire disclosure of these patents/applications is expressly incorporated herein by reference.

BACKGROUND

Pathologies of the gastro-intestinal ("GI") system, the biliary tree, the vascular system and other body lumens and hollow organs are commonly treated through endoscopic procedures, many of which require active and/or prophylactic hemostasis to reduce internal bleeding. Tools for deploying hemostatic clips via endoscopes are often used to stop internal bleeding by clamping together the edges of wounds or incisions.

In the simplest form, these clips grasp tissue surrounding a wound, bringing edges of the wound together to allow natural healing processes to close the wound. Specialized endoscopic clipping devices are used to deliver the clips to desired locations within the body and to position and deploy the clips at the desired locations after which the clip delivery device is withdrawn, leaving the clip within the body.

Endoscopic hemostatic clipping devices are generally designed to reach tissues deep within the body (e.g., within the GI tract, the pulmonary system, the vascular system or other lumens and ducts) via a working lumen of an endoscope. Thus, the dimensions of the clipping device are limited by the dimensions of the working channels of endoscopes with which they are to be employed.

SUMMARY OF THE INVENTION

In one aspect, the present invention is directed to a tissue clipping apparatus comprising a flexible, elongate member, a proximal end of which remains external to the body accessible to a user while a distal end of the flexible member is inserted into the body to a location adjacent to target tissue to be clipped. A control wire extending through the flexible member in combination with a capsule is releasably coupled to a distal end of the flexible member and a clip, a proximal portion of the clip being received within the capsule. A joint releasably coupling the clip to the control wire includes a yoke extending around a proximal end of the clip and a frangible link which fails when subject to a predetermined tension to separate the clip from the control wire.

BRIEF DESCRIPTION OF THE DRAWINGS

FIG. 3 is a cross-sectional view of a distal tip of a retainer for the clip of FIG. 1;

FIG. 4 is a perspective view of a retainer for the clip of FIG. 1;

FIG. 7 is a perspective view of a single piece hemostatic clip according to a second embodiment of the present invention;

FIG. 8 is a cross-sectional view of a shear pin according to a second exemplary embodiment of the present invention;

FIG. 11 is a perspective view of a clip according to a fourth exemplary embodiment of the present invention;

FIG. 12 is a perspective view of a deployed clip according to a fourth exemplary embodiment of the present invention;

FIG. 16a is a perspective view of the wire lock mechanism according to the present invention;

FIG. 16b is a close-up view of the wire lock mechanism according to the present invention; and FIG. 16c is a perspective view of a crushed wire lock mechanism according to the present invention.

DETAILED DESCRIPTION

Figure 1:
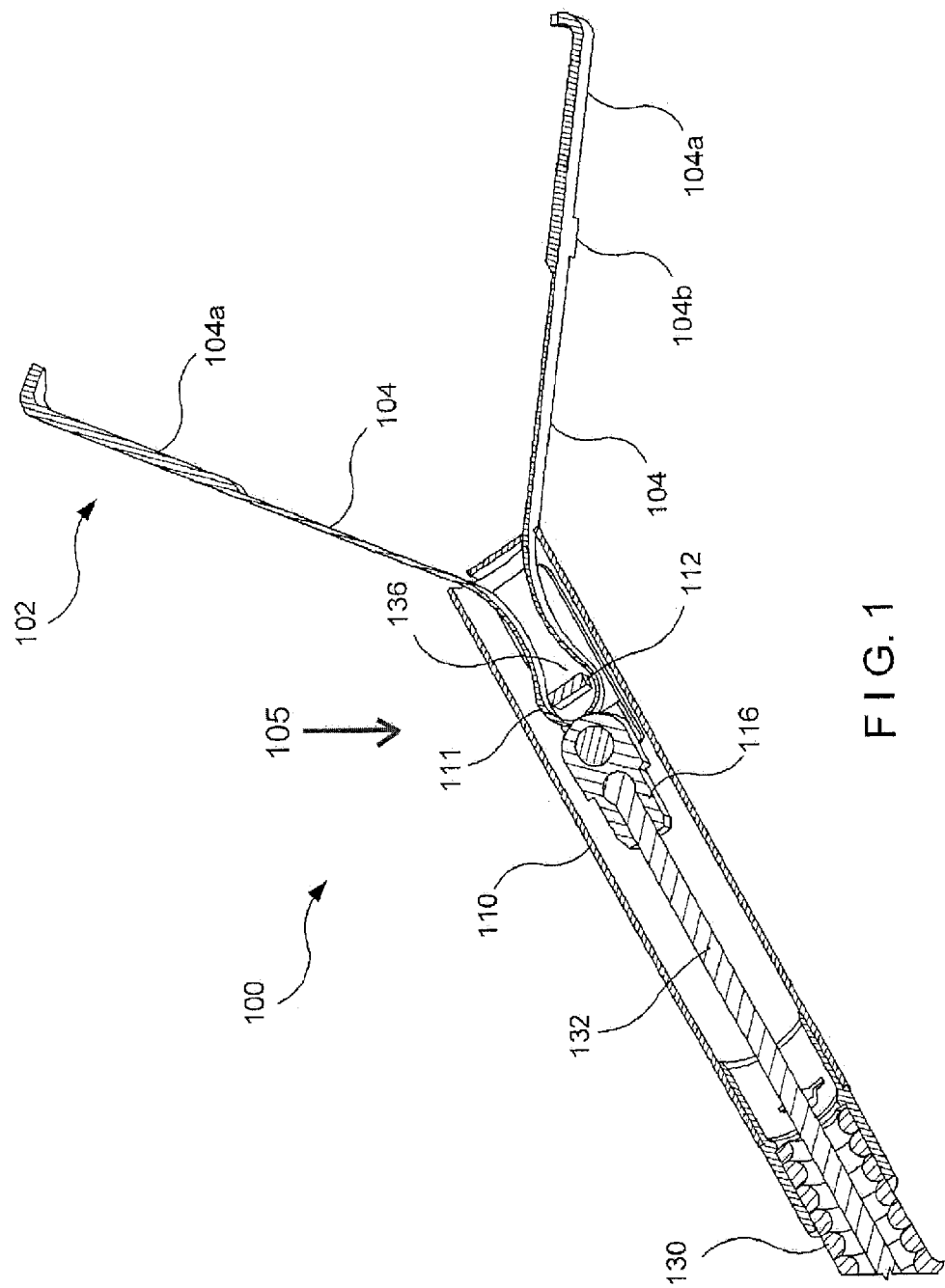
FIG. 1 is a cross-sectional view of a single piece hemostatic clip according to an embodiment of the present invention.

According to the embodiments of the present invention, a hemostatic clipping device is provided that is relatively simple to manufacture and use. Exemplary embodiments of the clipping device improve on the deployment mechanism for both single and two piece hemostatic clips as well as on the mechanism for tip-catheter separation. The embodiments also provide protection of the working channel of the endoscope from sharp edges of the clip deployment device. Examples of hemostatic clips currently employed in the field include clips such as those disclosed in U.S. Patent Application No. 60/915,806 entitled "Single Stage Hemostasis Clipping Device" filed on May 3, 2007 by Cohen et al. (hereinafter the '806 application), the entire disclosure of which is incorporated herein by reference.

As shown in FIGS. 1-4, a clipping device 100 according to an exemplary embodiment of the invention deploys from within a capsule 110 a single piece hemostatic clip 102 including a pair of tissue gripping arms 104 to clamp tissue to, for example, clamp a wound closed to stop bleeding. The hemostatic clip 102 is formed of a biocompatible material including metals such as stainless steel and Nitinol, polymers, biological materials and the like, as would be understood by those skilled in the art. During an initial insertion configuration, the clip 102 is contained within the capsule 110, constraining the arms 104 in a closed configuration with distal ends of the arms 104 in proximity to one another against a bias of the arms 104 which urges them apart into the open, tissue receiving configuration shown in FIG. 1.

Specifically, a proximal portion of the clip 102 is housed within the capsule 110 along with proximal and intermediate portions of the arms 104, wherein contact between the inner walls of the capsule 110 and the arms 104 draws the arms 104 closed against one another. A proximal portion of the capsule 110 is connected to a flexible member 130, which is formed, for example, as an elongated tubular structure extending to a proximal portion of the device 100 which remains outside the body at all times. The flexible member 130 may be formed as a coil or, alternatively, as any other suitable hollow, flexible structure. In an exemplary embodiment, the flexible member 130 is made of a suitably thin material which transmits to the distal end rotation applied in either direction to the proximal portion without substantially winding up. Specifically, rotation of the proximal portion of the device 100 about the longitudinal axis is transmitted along the flexible member 130 to the capsule 110 to position the clip 102 in an optimum orientation relative to a portion of tissue to be gripped thereby. A control wire 132 is slidably received within the flexible member 130 with a distal end thereof received within the capsule 110, as will be described in greater detail below. A proximal portion of the control wire 132 is connected to an actuator (not shown) on the proximal portion of the device 100 where it remains accessible to a user throughout the procedure.

Figure 2:
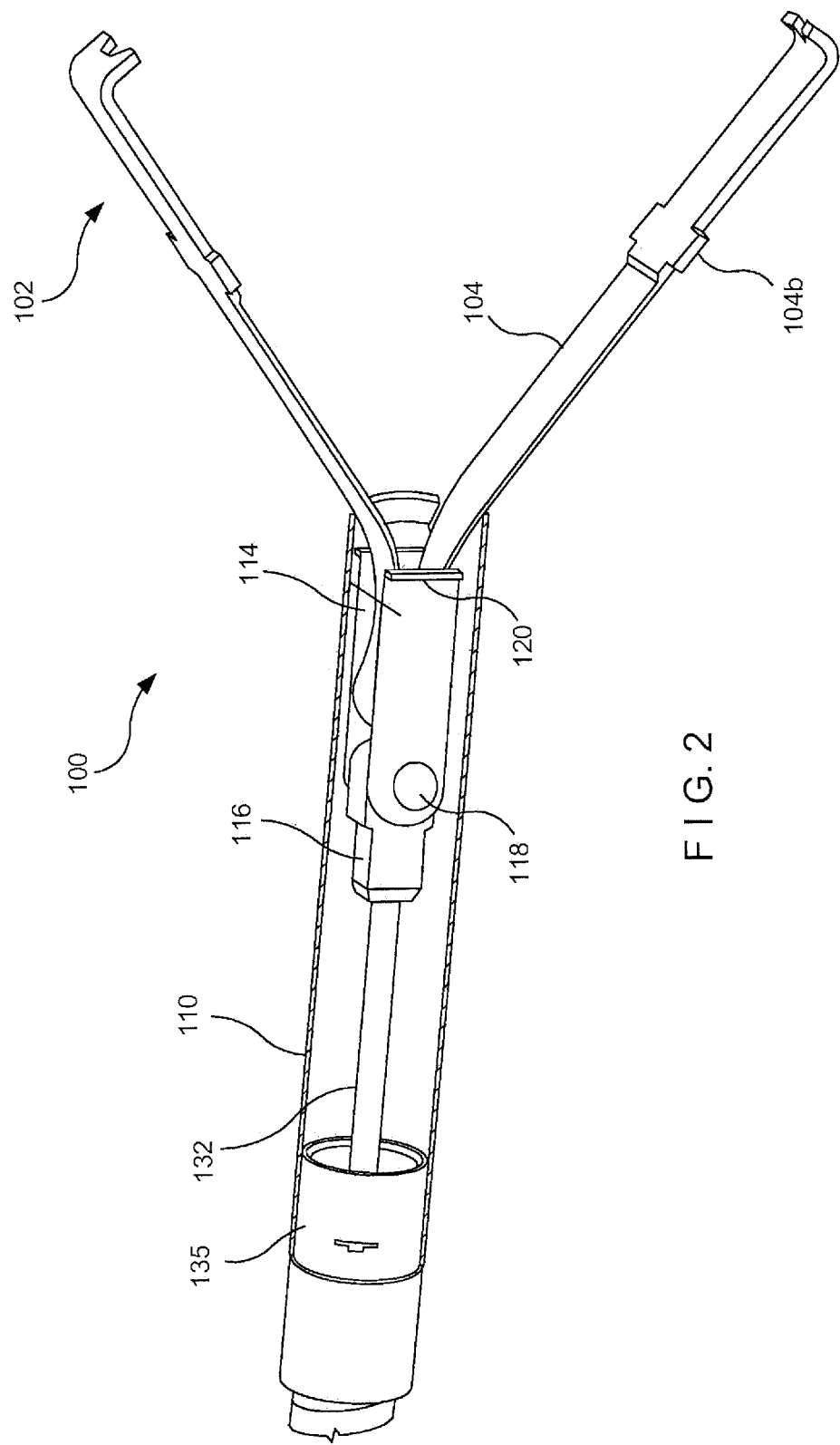
FIG. 2 is a perspective view a single piece hemostatic clip according to an embodiment of the present invention.
Figures 5, 6:
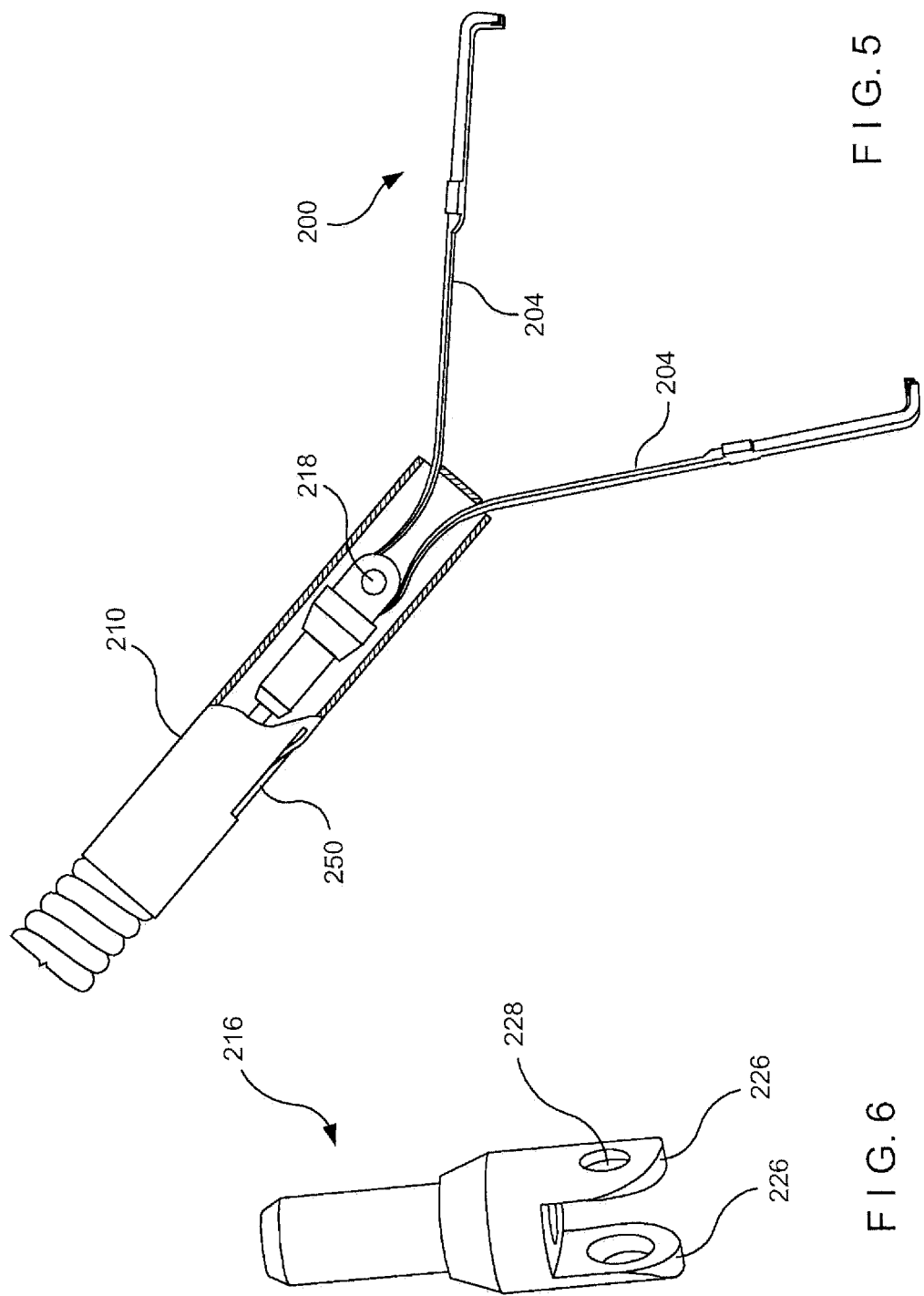
FIG. 5 is a perspective view of a single piece hemostatic clip according to a second embodiment of the present invention.
FIG. 6 is a perspective view of a clevis according to a second embodiment of the present invention.

A proximal portion of the clip 102 may be formed in a relatively hourglass shape with a bulbed proximal end 111. Specifically, a joint 105 is provided on the proximal portion of the clip 102 and comprises a yoke 114 removably engaging the clip 102 to the control wire 132. The bulbed shape of the proximal end 111 can maximize a clip-opening angle of the clip 102, as those skilled in the art will understand, while the hourglass shape forms a space 136 within the proximal end 111 for receiving therein a yoke post 112 of a deployment mechanism. The yoke post 112 may be coupled to the control wire 132 via a yoke 114 and a clevis 116 so that movement of the control wire 132 proximally and distally through the flexible member 130 facilitates contact between the yoke post 112 and the proximal end 111 and thus moves the clip 102 proximally and distally relative to the capsule 110. As would be understood by those skilled in the art, the shape of the yoke post 112 is not important so long as the yoke post 112 is strong enough to transmit the desired proximal and distal forces from the control wire 132 to the clip 102. Thus, the yoke post 112 may be formed in various geometries including, for example, rectangular, round or oval, etc. As would be understood by those skilled in the art, a proximal portion of the yoke 114 can be coupled to the clevis 116 via a shear pin 118 which is designed to fail when subject to a predetermined force, such as a tension exerted thereto via the control wire 132. As shown in FIGS. 2 and 3, the shear pin 118 may be formed, for example, as a substantially cylindrical pin extending through openings in the yoke 114 and the clevis 116 with ends thereof, in one embodiment, having a conical radius aiding in centering the clip 102 in the capsule 110. However, any other suitable shapes of the yoke 114 may be applied as well. In an alternate embodiment, the shear pin 118 may be coupled to one or both of the yoke 114 and the clevis 116 via an interference fit. The yoke 114 may include lateral walls which extend over sides of the clevis so that the shear pin 118 may pass on a line through both the yoke 114 and the clevis 116, as can be seen in the embodiment of FIG. 3. Each lateral wall of the yoke 114 may further comprise a centering boss 120 formed as a tabbed protrusion projecting radially outward therefrom. The centering boss 120 can be formed with a radius consistent with the inner diameter of the capsule 110 to center the clip 102 therein. A proximal end of the clevis 116 can be attached to a distal end of the control wire 132. In this embodiment, the distal end of the control wire includes a ball joint 133 which is received in a correspondingly sized and shaped recess of the clevis 116, coupling the clevis 116 to the control wire 132. Those skilled in the art will recognize that any number of attachment arrangements may be used to bond the control wire 132 to the clevis 116 so long as the attachment is capable of transmitting the desired force, such as tension from the control wire 132 to the clevis 116 and, consequently, to the yoke 112 and the clip 102. Thus, actuation of the control wire 132 distally and proximally can open and close the clip according as will be described in more detail below.

The clip 102 of the present invention may be opened and closed a plurality of times during a procedure so long as a proximal pull force exerted on the control wire 132 does not exceed a predetermined threshold which is designed to cause the shear pin 118 to fail, thus locking the clip 102 closed, as will be described in more detail below. Specifically, a user may open and close the clip 102 a plurality of times to properly situate the clip 102 over target tissue before locking the clip 102 in place. When a desired placement area has been reached, and it is desired to lock the clip 102 in place, the user may draw the control wire 132 proximally to draw the clip 102 into the capsule 110. Alternatively, the capsule 110 may be advanced distally to provide the force necessary to draw the clip 102 thereinto. The arms 104 gradually increase in width from a narrow proximal end to increased width shoulders 104b at a distal end so that, as the clip 102 is drawn proximally into the capsule 110, a point is reached at which the clip 102 is closed, with distal ends of the arms 104 coming together to grip tissue and the shoulders 104b engaging the distal end of the capsule 110 to prevent the clip 102 from being drawn further into the capsule 110. At this point, an additional pull force exerted on the control wire 132 increases the tension on the shear pin 118 until a failure level is reached. When this happens, the clevis 116 is separated from the yoke 112 and the clip 102 is locked in the closed configuration over any tissue gripped thereby. The clip 102 may employ a locking means known in the art. The shear pin 118 is made of a material such as a polymer or a metal such as tantalum, gold or silver, wherein the release force of the material is approximately 26.69-66.72 N. Alternatively, the release force may vary from 20-80 N. Thus, the clevis 116 and yoke 114 can be formed to have a strength greater than that of the shear pin 118. These items may be formed, for example, of Stainless Steel or a high strength polymer or thermoset. The fractured shear pin 118 is adapted to remain housed within the capsule 110, wherein a construction thereof ensures that fractured pieces thereof do not include sharp edges. In this manner, smaller fractured portions thereof pose no potential harm to a patient even if they escape the capsule 110.

As described in more detail in the '806 application, as the freed clevis 116 is pulled proximally, it engages a distal face of a bushing support 135, driving the bushing support 135 proximally into a bushing 134 at the distal end of the flexible member 130. When received within the proximal end of the capsule 110, the bushing support 135 engages at least one tab (not shown) of the bushing 134 urging the tab radially outward into engagement with corresponding windows (not shown) of the capsule 110. The tabs of the bushing are biased toward a radially inward position out of engagement with the windows of the capsule 110 so that, when the bushing support 135 is dislodged from the proximal end of the capsule 110, the tabs of the bushing 134 are freed to disengage the windows of the capsule and the capsule 110 is permanently separated from the bushing 134 and the flexible member 130, leaving the clip 102 locked on the gripped tissue. The flexible member 130 may then be withdrawn from the body.

In an alternate embodiment, instead of the bushing support 135, the capsule 110 may be maintained in engagement with the bushing 134 by a retainer 140 formed at the distal end of the bushing 134. The retainer 140 may include tabs 146 which engage corresponding windows (not shown) in the capsule 110 (or, alternatively, by a friction fit). The retainer 140 may comprise an opening 142 sized to slidably receive the control wire 132 therein with a slot 143 allowing the retainer 140 to be slid in place over the wire 132. The slot 143 is sized to allow the retainer 140 to be clipped onto the control wire 132, thus obviating the need to thread the control wire 132 through the retainer 140. The retainer 140 may further comprise two spring arms 144, each of which may include a tab 146 biased to engage the corresponding window of the capsule 110. Then, when the shear pin 118 fails and the clevis 116 is drawn proximally as described above, the clevis 116 can drive the retainer 140 into the bushing 134, drawing the tabs 146 out of engagement with the capsule 110 and freeing the capsule 110 from the flexible member 130 in a manner similar to that described earlier. The flexible member 130 may then be withdrawn from the body. In one embodiment, the retainer 140 is composed of a metal that can be tempered, such as 17-7 Stainless Steel. However, it is noted that the retainer 140 may be made of numerous biocompatible materials including biocompatible metals and formable polymers without deviating from the spirit and scope of the present invention.

As shown in FIGS. 5-8, a clip 200 according to a further embodiment of the invention, comprises a relatively hourglass-shaped proximal portion sized to engage a clevis 216 in a capsule 210 in a manner substantially similar to that described above in regard to the device 100. However, in this embodiment, the yoke and clevis have been replaced by a unitary clevis 216 with arms 226 of the clevis 216 extending around the proximal end of the clip 200 so that a shear pin 218 received through openings 228 of the clevis 216 extends into the hourglass-shaped proximal portion of the clip 200 in a manner similar to the yoke post 112 of the device 100. The clip 200 may be coupled to a control wire 232 in a manner similar to that described for the device 100. Furthermore, the connection between a flexible member 230 and the capsule 210 and the mechanism for separating the capsule 210 from the flexible member 230 may also be substantially similar to that described for the device 100.

The capsule 210 may be formed with clip retaining tabs 250 at a proximal portion thereof to hold the clip 200 in place within the capsule 210 after deployment, thus locking the clip 200 in the closed configuration. Specifically, during deployment, the clip 200 is retracted proximally by a predetermined distance into the capsule 210, drawing the hourglass-shaped proximal portion of the clip 200 proximally past a proximal end of the tabs 250 and a decreased thickness portion 252 of the clip 200 distally of the hourglass-shaped proximal portion, adjacent to the tabs 250. This movement permits the tabs 250 to spring radially inward so that contact between the proximal ends of the tabs 250 and the hourglass-shaped proximal portion of the clip 200 locks the clip 200 in the capsule 210 and prevents the clip 200 from re-opening. Furthermore, although a holding force applied by the clip retaining tabs 250 is substantial enough to retain the clip 200 therein after deployment, it is preferably selected so that a distal force, such as a compression force applied to the control wire 232 may move the hourglass-shaped proximal portion distally past the tabs 250 enabling a user to reopen the clip (e.g., for repositioning) at any time before the control wire 232 is separated from the clevis 216.

As described above, arms 204 of the clip 200 are provided with shoulders 204b defining an increased thickness portion 204a which prevent the clip 200 from being pulled into the capsule 210 beyond a predetermined length. Thus, when the clip 200 has been drawn into the capsule 210 by this distance, additional pulling force applied to the control wire increases a tension thereon until the fail level of the shear pin 218 is reached as described above. As shown in FIG. 8, the shear pin 218 may, for example, be provided with one or more stress concentrators 258 formed as grooves formed along the outer diameter thereof, the stress concentrators 258 defining a weaker point along the length of the shear pin 218. Those skilled in the art will understand that the size and number of these stress concentrators may be varied to obtain any desired fail level of the shear pin 218.

Figure 9:
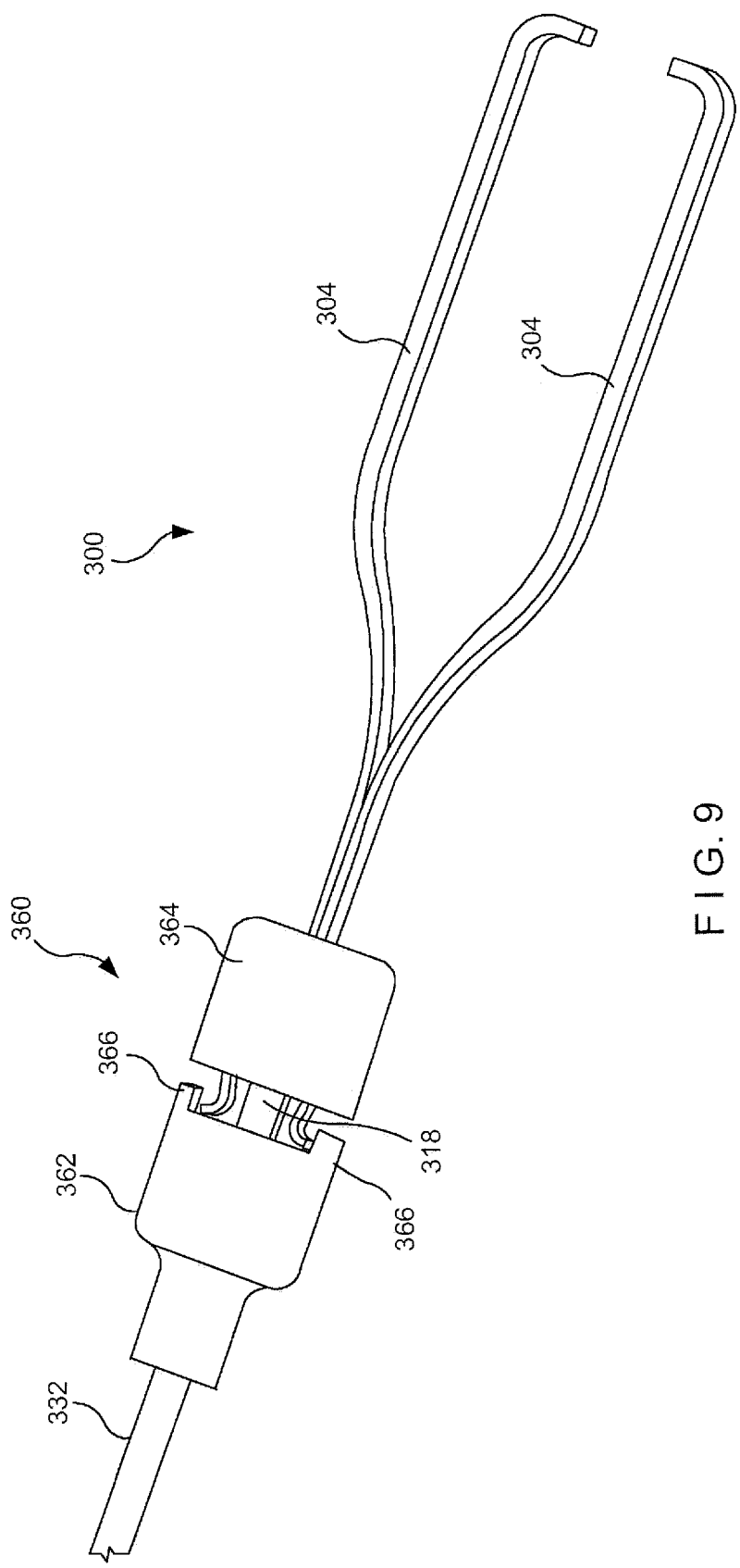
FIG. 9 is a perspective view of a clip according to a third exemplary embodiment of the present invention.
Figure 10:
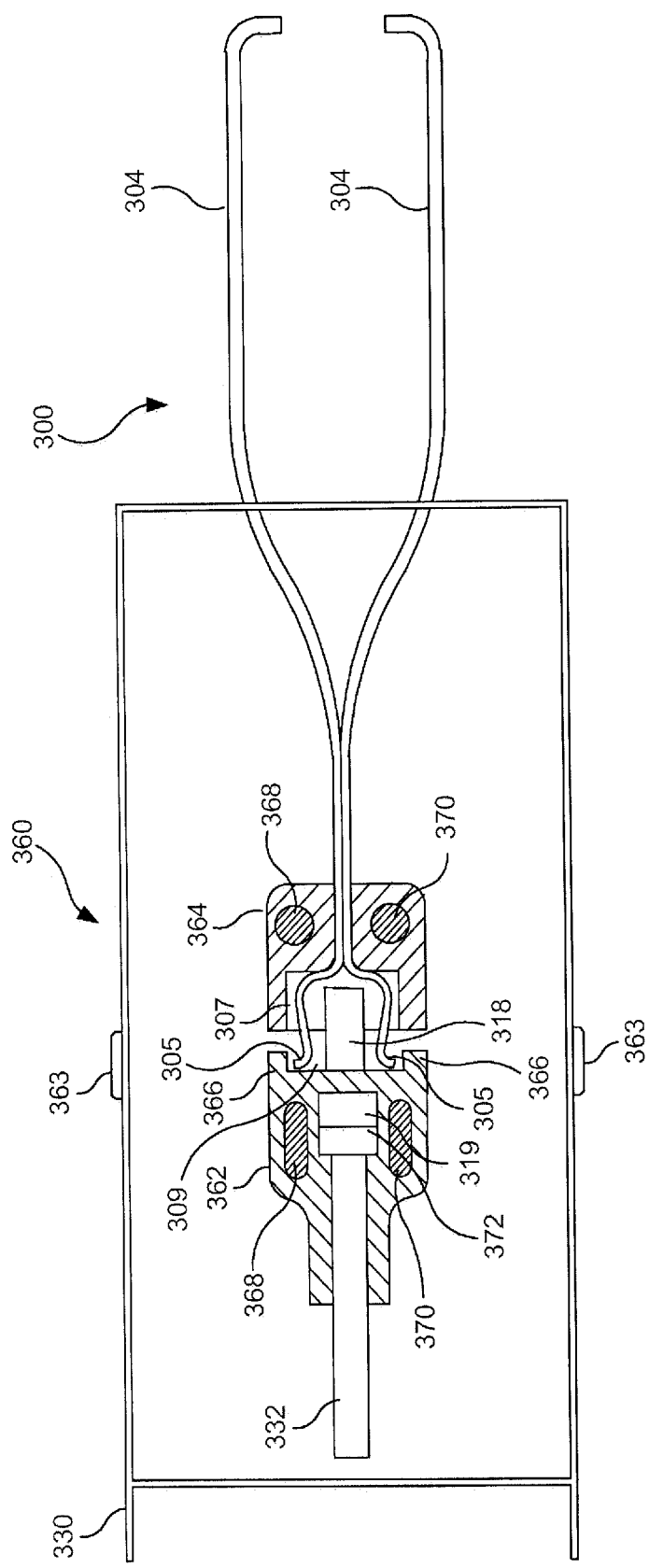
FIG. 10 is a partial cross sectional view of a clip according to a third exemplary embodiment of the present invention.
Figure 13:
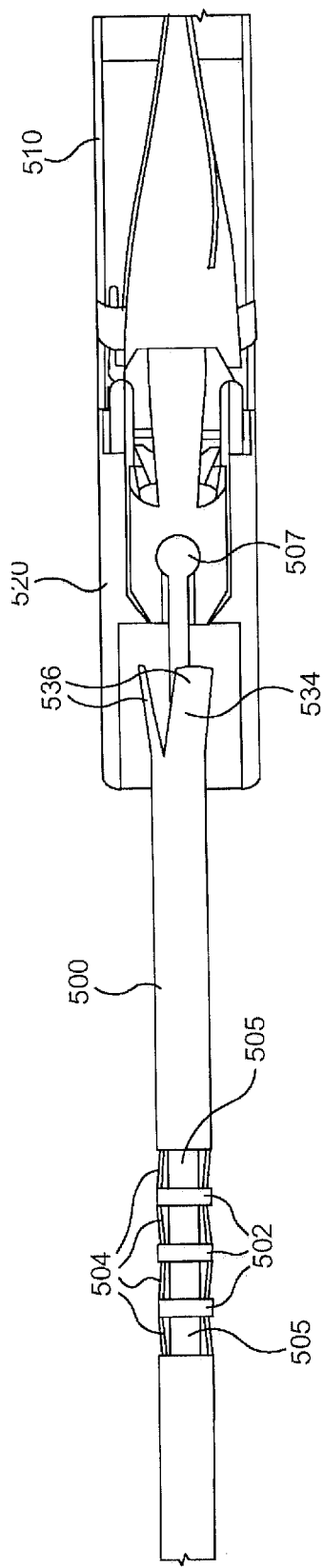
FIG. 13 is a perspective view of a wire lock mechanism according to an embodiment of the present invention.
Figure 14:
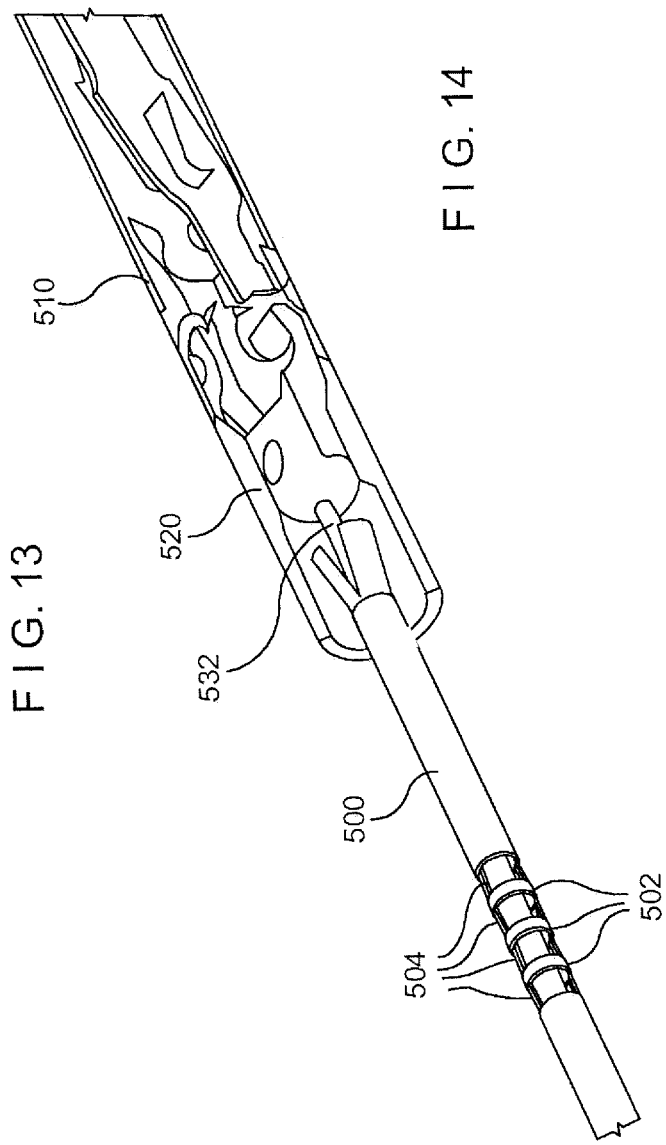
FIG. 14 is a second perspective view of the wire lock mechanism according to an embodiment of the present invention.
Figure 15:
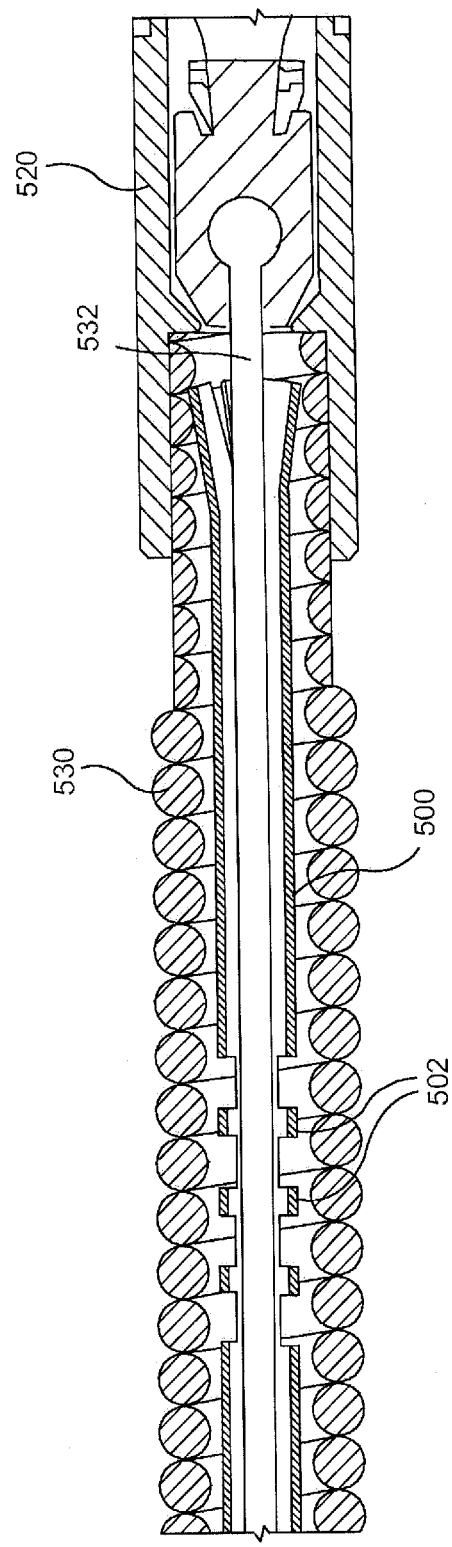
FIG. 15 is a cross sectional view of the wire lock mechanism according to an embodiment of the present invention.

As shown in FIGS. 9 and 10, a clip 300 according to another exemplary embodiment of the invention can be releasably attached at a proximal end to a shell 360. The shell 360 may comprise proximal and distal halves 362, 364, respectively, releasably attached to one another. A proximal end of the proximal half 362 can be attached to a control wire 332. The proximal half 362 may be formed as two complementary pieces which are assembled over the distal end of the control wire 332. For example, a first one of the pieces of the proximal half 362 may include one or more male posts 368, while the other piece includes a corresponding set of female holes 370 which aid in aligning the pieces with one another and bonding the pieces together (e.g., via adhesive) to form the proximal half 362. Similarly, the distal half 364 may be formed as two pieces which are assembled over the proximal end of the clip 300 with a similar set of complementary male posts 368 and female holes 370 to align the pieces when assembled (e.g., via adhesive) as the distal half 364. Those skilled in the art will understand that the pieces of the proximal and distal halves 362, 364, respectively, may be formed by, for example, injection molding. Specifically, each of the proximal half 362 and distal half 364 in this embodiment can be formed from a pair of complementary semi-cylindrical pieces, attached to one another using the male posts 368 and female holes 370 as references. Furthermore, the male posts 368 and female holes 370 may serve as energy directors for ultrasonic welding, as those skilled in the art will understand.

The clip 300 may comprise two arms 304, each comprising a proximal portion extending radially outward and contained within a capsule 360, as shown in FIGS. 9 and 10. It is noted that although exemplary embodiments of the present invention are disclosed as having two arms, any plurality of arms may be employed without deviating from the spirit and scope of the present invention. The clip 300 is further provided with shoulders (not shown) which prevent the clip 300 from being retracted into a capsule 360 beyond a predetermined distance as described above in regard to the embodiments of FIGS. 1-8. A large cavity 307 is formed in the proximal end of the distal half 364 while a corresponding cavity 309 is formed in the distal end of the proximal half 362. The cavities 307, 309 receive proximal ends of the arms 304 and constrain them to remain therein against a bias which urges the proximal ends of the arms 304 and tabs 305 formed thereby radially outward.

Movement of the clip 300 is controlled by the control wire 332, which extends through a flexible member 330 in the same manner described above out of the body to a proximal portion accessible to a user. A distal end of the control wire 332 may include an increased diameter portion such as a sphere or cylinder is received within a correspondingly sized and shaped recess 372 at the end of a lumen in the proximal half 362 sized to receive the distal portion of the control wire 332. Thus, the proximal half 362 can be coupled to the control wire 332 for movement proximally and distally therewith. A center post 318, which may extend proximally from a proximal end of the distal half 364, may include an increased diameter portion 319 at a proximal end thereof. The proximal end of the post 318 may be coupled to side walls of the cavity 307 to bind the center post 318 to the distal half 364. The increased diameter portion 319 may be inserted into the recess 372 before the pieces of the proximal half 362 are bonded to one another in the same manner as the distal end of the control wire 332. Thus, the post 318 can bind the proximal and distal halves 362, 364 to one another The recess 372 may also be sized to receive the distal end of the control wire 332 and the proximal end of the center post 318 with a substantial friction fit to prevent unwanted movement of the respective elements therein. Those skilled in the art will recognize that the control wire 332 and the post 318 may be coupled to the proximal half 364 in any number of ways (e.g., with separate recesses 372) including, but not limited to, welding, bonding, melting, etc.

During insertion, the clip 300 can be partially retracted into the shell 360, causing the arms 304 to approach one another. Upon reaching a target tissue site, a distal compressive force may be applied to a control wire 332, which translates the force to the center post 318, the force being further translated to the distal half 364 of the shell 360, thereby pushing the clip 300 out of the shell and causing the arms 304 to expand radially away from one another. When target tissue is received between the arms 304, the control wire 332 can be withdrawn proximally while maintaining the flexible member 330 and the capsule 360 substantially immobile so that the clip 300 is retracted into the shell 360 drawing the arms 304 toward one another. After the shoulders (not shown) have engaged the capsule 360 to prevent further withdrawal of the clip 300 thereinto, additional proximally directed force applied to the control wire 332 increases tension on the control wire 332 and, consequently, on the post 318 until a failure level of the post 318 is exceeded. In one embodiment, the center post 318 is composed of a material similar to that of the shear pin 118 formed to fail at approximately 26.69-66.72 N, as those skilled in the art will understand. Alternatively, the center post 318 may be formed of another suitable material and/or geometry. When the post 318 fails, the proximal and distal halves 362, 364 can be separated from one another, and the tabs 305 which are no longer constrained by the walls of the cavity 309 of the proximal half 362 can spring outward and engage corresponding features of the capsule 360 (e.g., windows 363) to lock the clip closed and keep it in position within the capsule 360.

As shown in FIGS. 11 and 12, a clip 400 according to another exemplary embodiment of the invention may include arms 404 residing in a capsule 410. The arms 404 bend along a curve to bias the proximal and distal ends thereof radially away from one another in a manner similar to that of the embodiment of FIGS. 9 and 10. Curves of the proximal portions of the arms 404 may form a pocket 408 while the distal ends of the arms 404 are formed in a manner substantially similar to that of the previously described embodiments. Proximal ends of the arms 404 may contain openings 406 through which a wire loop 418 may pass to couple the clip 400 to a control wire 432. Those skilled in the art will recognize that the openings 406 may be formed as rounded openings with smoothed edges to prevent unwanted trauma to the wire loop 418. In assembly, an end of the wire loop 418 can be passed through the openings 406 and the two ends of the wire loop 418 can be coupled to the distal end of the control wire 432 using, for example, a wire mate 416 compressed thereover. For example, the wire mate 416 may comprise a section of hypotube crushed over the wire loop 418. Alternatively, as would be understood by those skilled in the art, the wire mate 416 may be coupled to the wire loop 418 and the control wire 432 by staking, bonding, welding or any other known method. In the initial configuration, the wire loop 418 can be bound with a minimal clearance, thereby gripping the proximal ends of the arms 404 tightly against one another against the bias of the arms 404 urging the proximal ends of the arms 404 radially outward away from one another. In yet another embodiment (not shown), the control wire 432 may be formed as a single continuous wire extending from a proximal portion accessible to a user to a distal portion joined to the openings 406 with no mating portions at a distal portion thereof.

In the same manner described above, the control wire 432 may be manipulated to position the clip 400 over a target portion of tissue. As the clip 400 is urged distally out of the capsule 410, the bias of the arms 404 moves the distal ends thereof away from one another to an open tissue receiving configuration. When the target tissue is received between the distal ends of the arms 404, the control wire 432 may be drawn proximally to retract the clip 400 into the capsule 410 bringing the distal ends of the arms 404 together to grip the tissue therebetween. As the clip 400 enters the capsule 410, shoulders (not shown) of the arms 404 may contact the capsule 410 preventing further entry of the clip 400 into the capsule 410. Additional proximally directed force applied to the control wire 432 after this point increases tension in the control wire 432 until the wire loop 418 fails, releasing the proximal ends of the arms 404 to spring radially outward away from one another allowing tabs 414 to engage windows 412 of the capsule 410, locking the clip 400 closed and maintaining the clip 400 in the capsule 410. The wire mate 416 now moves proximally to disengage the capsule 410 from a flexible member (not shown) using a mechanism similar to any of those described in the previous embodiments.

As shown in FIGS. 13-16, any of the above embodiments may include a locking mechanism which will lock the control wire and any components coupled to the distal end thereof within the distal end of a bushing or flexible member as described above. This should prevent a user from moving the severed control wire distally out of the distal end of the flexible member or bushing after the clip has been deployed to safeguard against injuries that may be caused by contact with the control wire or any components (e.g., proximal half 364) attached thereto.

Specifically, a closeable or crushable wire lock 500 is disclosed which may provide a streamlined system to more safely remove these components from the body. The closeable wire lock 500 is intended to prevent pushing the sharp, sheared control wire into the anatomy for safety reasons. The closeable wire lock 500 of the present invention may be used to forcibly separate the capsule 510 from a bushing 520 attached to a flexible member 530, the bushing 520 adapted to be separatable from the capsule 510 via a retainer or other mechanism as disclosed with reference to FIGS. 1-4. Specifically, the closeable wire lock 500 may be particularly useful in cases where all other frangible links between the capsule 510 and bushing 520 have been broken. Furthermore, the closeable wire lock 500 may be employed in any of the clip deployment mechanisms disclosed herein.

With reference to FIGS. 13-16, a closeable wire lock 500 can be formed as a tube slidably receiving therein a control wire 532. A closeable section of the lock 500 may include a series of hubs 502 coupled to one another by a series of struts 504 and separated from one another by a series of openings 505. It is noted that although the present embodiment is disclosed with three hubs 502 and four struts 504, any number of hubs 502 and struts 504 may be employed herein without deviating from the spirit and scope of the present invention. As in the embodiments described above, a control wire 532 may extend through the lock 500 to a distal end comprising, for example, a ball and socket joint within a bushing 520. When the control wire 532 is separated from the clip and moves proximally through the capsule, the ball 507 is adapted to enter an enlarged distal end 534 of the lock 500 formed, for example, as a series of fins 536 separated from one another and bent slightly radially outward. As the ball 507 moves proximally into the end 534 of the lock 500, the fins 536 can grip the ball 507 preventing relative movement between the control wire 532 and the lock 500. Further proximally directed force applied to the control wire 532 should draw the ball 507 pushes the lock 500 proximally. A proximal end (not shown) of the lock 500 can be immovably coupled to the flexible member 530 so that this proximally directed force applied to the control wire 532 compresses the lock 500 causing the struts 504 to bend radially outward moving the hubs 502 toward one another as the openings 505 are closed. When bent outward, the struts 504 engage spaces between the coils of the flexible member 530 preventing relative movement between the lock 500 and the flexible member 530. Thus, the control wire 532 can be locked within the distal end of the flexible member 530 and can not be advanced distally therefrom to cause injury.

Clip and clip deployment mechanisms according to the present invention may be designed in a wide variety of sizes for applications such as wound closure, hemostasis, tissue bunching (e.g., to alter the size or shape of a hollow organ) or as fasteners to join tissue. Alternatively, clips according to the present invention may be used to anchor items to tissue. Accordingly, although the present invention has been disclosed with specific designs and applications, it is noted that a variety of designs may be employed therein without deviating from the spirit and scope of the present invention. For example, a predisposed bias of a clip according to the present invention may be formed to lie at a midpoint between the fully open and fully closed configurations. In this manner, the stress to which the clip is subjected in each of these configurations is minimized, enabling the clip to be made more flexible. The specification and drawings are, therefore, to be regarded in an illustrative rather than a restrictive sense.

What is claimed is:

1. A tissue clipping apparatus, comprising:
    a flexible insertion member extending from a proximal end which, in an operative configuration, remains outside a body accessible to a user to a distal end which is inserted into the body through a naturally occurring body lumen;
    a clip including first and second clip arms, the first and second clip aiiiis bent along a curve to bias proximal and distal ends thereof radially away from one another, curves of proximal portions of the first and second clip arms forming a tissue receiving pocket between the first and second clip arms;
    a capsule housing a portion of the clip therein;
    a control wire extending through the insertion member from a proximal end to a distal end, the control wire operable to move the first and second clip arms between an open configuration in which distal ends of the first and second clip arms are separated from one another and a closed configuration in which the distal ends of the first and second clip arms are drawn together to grip tissue located therebetween, the first and second clip aims being configured to be moved repeatedly between the open and closed configurations until the clip is deployed;
    a joint releasably coupling the distal end of the control wire to the first and second clip arms, the joint being released from the first and second clip arms to lock the first and second clip arms in the closed configuration when a pull force exerted on the control wire exceeds a predetermined level; and
    a releasable coupling between the capsule and the insertion member, the coupling including at least one engagement member,
    wherein, when the joint is released, the at least one engagement member is drawn radially inward through an opening in the capsule to release the capsule from the insertion member.

2. The apparatus of claim 1, wherein the joint is configured to maintain the proximal ends of the first and second clip arms in a radially inward position out of engagement with an inner surface of the capsule, the joint configured so that, when the joint is released, the joint is separated from the first and second clip aims releasing the proximal ends of the first and second clip arms to spring radially outward to engage a portion of the capsule locking the first and second clip arms in the closed configuration.

3. The apparatus of claim 1, wherein the joint includes a clevis extending distally from the control wire, the clevis including a first arm extending within the capsule on a first side of a proximal portion of the first and second clip arms and a second arm extending within the capsule on a second side of the proximal portions of the first and second clip arms, the first and second arms of the clevis being coupled to the first and second clip arms via a cross pin that passes through the first and second clip arms.

4. The apparatus of claim 3, wherein the clevis is formed so that, when the joint is released, the clevis moves proximally out of the capsule disengaging the capsule from the insertion member as the engagement member is drawn radially inward through the opening in the capsule.

5. The apparatus of claim 1, wherein the first clip atm includes a locking tab at the proximal end thereof and the capsule includes a locking feature configured to lockingly engage the locking tab when the joint is released.

6. The apparatus of claim 1, wherein the joint includes a wire loop.

7. The apparatus of claim 6, wherein a proximal portion of each of the first and second clip arms includes an opening through which the wire loop is passed to couple the control wire to the clip.

8. The apparatus of claim 1, further comprising a locking mechanism configured to lock the control wire within the distal end of the flexible insertion member once the joint is separated.

9. The apparatus of claim 1, further comprising a bushing coupled to a distal end of a flexible sheath and releasably coupled to a proximal end of the capsule.

10. The apparatus of claim 9, wherein the flexible sheath is formed as a coil defining a lumen through which the insertion member extends, a proximal end of the hushing being coupled to a distal end of the coil.

11. A method for treating tissue, comprising:
inserting a clip to a target area within a living body adjacent target tissue, the clip including first and second clip arms bent along a curve to bias proximal and distal ends thereof radially away from one another, curves of proximal portions of the first and second clip arms forming a tissue receiving pocket therebetween;
moving a control member coupled to the clip distally to move the clip from a closed configuration to an expanded configuration, wherein the control member is coupled to the clip via a separable joint, the joint maintaining the proximal ends of the first and second clip arms in a radially inward position out of contact with an inner surface of a capsule, the joint configured to be separated from the first and second clip arms when subjected to a predetermined force by the control member;
positioning the clip so that target tissue to be clipped is positioned between the distal ends of the first and second clip arms;
moving the control member proximally to draw the first and second clip arms to the closed configuration to grip the target tissue; and
exerting an additional proximal force on the control member to separate the joint from the first and second clip arms, separating the clip from the control member.

12. The method of claim 11, wherein the joint includes a wire loop.

13. The method of claim 12, wherein a proximal portion of the first and second clip arms includes an opening through which the wire loop is passed to couple the control member to the clip.

14. The method of claim 11, wherein the first clip arm includes a locking tab at the proximal end thereof.

15. The method of claim 14, wherein the capsule includes a locking feature configured to lockingly engage the locking tab when the joint is separated from the first clip arm to lock the clip within the capsule with the first and second clip arms in the closed configuration.

* * * * *